United States Patent [19]

Kock et al.

[11] Patent Number: 4,551,191

[45] Date of Patent: Nov. 5, 1985

[54] METHOD FOR UNIFORMLY DISTRIBUTING DISCRETE PARTICLES ON A MOVING POROUS WEB

[75] Inventors: Ronald W. Kock; John A. Esposito, both of Cincinnati, Ohio

[73] Assignee: The Procter & Gamble Company, Cincinnati, Ohio

[21] Appl. No.: 625,932

[22] Filed: Jun. 29, 1984

[51] Int. Cl.$^4$ .............................................. B29F 3/00
[52] U.S. Cl. ..................... 156/276; 156/209; 156/279; 156/285; 156/553; 118/308; 118/312; 427/108
[58] Field of Search ............... 156/276, 279, 381, 284, 156/285, 283, 552, 553, 209; 118/308, 312; 427/108

[56] References Cited

U.S. PATENT DOCUMENTS

| | | |
|---|---|---|
| 56,558 | 7/1866 | Hendley . |
| 430,707 | 6/1890 | Strahan . |
| 1,785,944 | 12/1930 | Ezdorf et al. . |
| 2,049,700 | 8/1936 | Gustafsson ...................... 299/140.1 |
| 2,196,808 | 4/1940 | Hawley, Jr. ........................ 156/276 |
| 2,294,899 | 9/1942 | Fourness et al. .................... 128/284 |
| 2,341,036 | 2/1944 | Guibert ................................. 91/45 |
| 2,476,465 | 7/1949 | Tarrant ................................. 275/2 |
| 2,569,765 | 10/1951 | Kellet et al. ......................... 156/276 |
| 2,577,205 | 12/1951 | Meyer et al. ..................... 156/276 X |
| 2,645,529 | 7/1953 | Jenner .................................. 302/12 |
| 2,975,543 | 3/1961 | Funk .................................. 43/148 |
| 3,002,849 | 10/1961 | Harmon et al. ....................... 117/21 |
| 3,084,874 | 4/1963 | Jones et al. .......................... 239/424 |

List continued on next page.

FOREIGN PATENT DOCUMENTS 108637 5/1984 European Pat. Off. .
2122538 1/1984 United Kingdom .

OTHER PUBLICATIONS

Pending U.S. patent application Ser. No. 563,339, filed 12/20/1983 in the name of Kramer et al. (commonly assigned).

*Primary Examiner*—David Simmons
*Attorney, Agent, or Firm*—E. Kelly Linman; John V. Gorman; Richard C. Witte

[57] ABSTRACT

The present invention comprises method and apparatus for substantially uniformly distributing a layer of discrete particles along a predetermined portion of the uppermost surface of a moving porous web so that the particles occupy less than 100% of the predetermined portion of the uppermost surface of said moving web. The method preferably comprises the steps of (a) entraining the particles into a moving gaseous stream;

(b) passing the gaseous stream through a conduit having a discharge end with a nozzle exit positioned adjacent the uppermost surface and oriented so as to discharge the gaseous stream containing said entrained particles in a direction substantially parallel to the direction of travel of the moving porous web;

(c) mixing the particles entrained in the gaseous stream inside the conduit to provide a substantially uniform distribution of the particles, as measured across the width of the nozzle exit of said conduit in a direction perpendicular to the direction of travel of said moving porous web;

(d) discharging the gaseous stream containing the uniformly distributed entrained particles from the conduit adjacent the predetermined portion of the uppermost surface of the moving porous web; and (e) maintaining the fluid pressure adjacent the lowermost surface of the moving porous web at a level lower than that adjacent the uppermost surface of the web in an area coinciding in width to the predetermined portion of the web, said area being located near the nozzle exit of the conduit, whereby the bulk of the uniformly distributed particles entrained in the discharged gaseous stream are substantially uniformly deposited onto the predetermined portion of the uppermost surface of the moving porous web as the bulk of the gas in the gaseous stream is drawn from the uppermost to the lowermost surface of said porous web.

50 Claims, 4 Drawing Figures

U.S. PATENT DOCUMENTS

| | | | |
|---|---|---|---|
| 3,271,215 | 9/1966 | Hoffman | 156/276 X |
| 3,378,174 | 4/1968 | Tunnell | 222/193 |
| 3,414,444 | 12/1968 | Bobkowicz | 156/279 X |
| 3,434,865 | 3/1969 | Doquire et al. | 428/108 |
| 3,447,723 | 6/1969 | Peterson et al. | 222/193 |
| 3,590,318 | 6/1971 | Probst et al. | 317/3 |
| 3,606,097 | 9/1971 | Wall | 222/176 |
| 3,671,284 | 6/1972 | Uhrig | 117/21 |
| 3,682,738 | 8/1972 | Smith | 156/283 |
| 3,715,076 | 2/1973 | Kenderi | 239/8 |
| 3,799,438 | 3/1974 | Shockley | 239/8 |
| 3,888,257 | 6/1975 | Cook et al. | 128/296 |
| 3,948,443 | 4/1976 | Omdal et al. | 239/8 |
| 4,055,180 | 10/1977 | Karami | 128/287 |
| 4,260,443 | 4/1981 | Lindsay et al. | 156/220 |
| 4,280,419 | 7/1981 | Fischer | 111/80 |
| 4,301,763 | 11/1981 | Goldstone | 118/308 |
| 4,344,986 | 8/1982 | Henery | 427/180 |
| 4,360,021 | 11/1982 | Stima | 128/287 |
| 4,410,324 | 10/1983 | Sabee | 604/368 |
| 4,414,255 | 11/1983 | Tokuyama et al. | 428/154 |

METHOD FOR UNIFORMLY DISTRIBUTING DISCRETE PARTICLES ON A MOVING POROUS WEB

TECHNICAL FIELD

The present invention relates to a method for substantially uniformly distributing a layer of discrete particles along a predetermined portion of the uppermost surface of a moving porous web. The present invention relates particularly to such a method wherein the particles occupy less than 100% of a predetermined portion of the uppermost surface of said moving web.

The present invention has particular relation to a method for substantially uniformly distributing a layer of discrete particles comprised of superabsorbent polymeric material onto a predetermined portion of the uppermost surface of a moving web of absorbent material, such as a tissue ply, a layer of airlaid comminuted wood pulp fibers, a three-dimensional absorbent batt or the like. In a particularly preferred embodiment, the particle lay down process is followed by superposing a second moving web of porous material, such as a tissue ply or the like, and three-dimensionally embossing said webs to form a uniformly three-dimensional absorbent laminate structure.

BACKGROUND OF THE INVENTION

Method and apparatus for distributing particulate over a given substrate are generally known in the art.

Typical applications for such method and apparatus are found in the field of agriculture where particulate spreaders are utilized to deposit seed and fertilizer.

Other prior art applications include the distribution of particulate in the form of gravel and/or de-icing compounds onto the surfaces of roadways during periods of inclement weather. Still other applications include the delivery of a powder coating reactant to the surface of a glass sheet while the glass sheet is maintained in an oxidizing atmosphere at a temperature sufficient to pyrolize the coating reactant to deposit a metal oxide film on the surface of the glass. One such method is disclosed in U.S. Pat. No. 4,344,986 issued to Henery on Aug. 17, 1982. In the disclosed embodiment, Henery employs a screw feeder for the reactant powder and an eductor to entrain the powder into a gaseous stream. A series of baffles project into the entrance of the coating chamber to create turbulence in the power/gas mixture, thereby allegedly improving the uniformity of coating. The discharge of the slotted nozzle is oriented substantially perpendicular to the surface of the glass sheet, which preferably moves beneath the nozzle to provide a complete coating by the discharged powder.

Recent advances in the field of absorbent structures such as disposable diapers have, however, given rise to a need for method and apparatus to substantially uniformly distribute discrete particles within a predetermined portion of the absorbent cores utilized in such structures so that the particles occupy less than 100% of the area in which they are distributed.

Although prior art absorbent structures useful as absorbent cores in products such as disposable diapers, incontinent pads, catamenial products, and the like have generally been comprised primarily of absorbent fibrous materials such as absorbent papers, absorbent cloths, fibrous batts, and the like, a relatively new class of compounds commonly known as superabsorbent polymers have been developed and are gaining increasing use as at least a part of such absorbent structures. Such superabsorbent polymers are normally water insoluble polymeric materials capable of absorbing at least 15 times their weight of water. Such superabsorbent polymers are available in a variety of forms, including flakes, powders and granules. Superabsorbent polymers generally differ from many conventional absorbent materials in that once an aqueous fluid is absorbed by most superabsorbent polymers, it generally cannot be expressed from the superabsorbent polymer under moderate pressure. This is often highly desirable in an absorbent structure such as a disposable diaper in that it prevents absorbed fluid from being expressed out of the structure.

When most superabsorbent polymers absorb aqueous fluids, they swell substantially, often to double their dry dimensions or more at saturation. At most superabsorbent polymers absorb fluid and swell, they generally become a gelatinous mass. If the superabsorbent polymer is in a particulate form and the particles are close to one another, they can coalesce and form a gel barrier which can block the flow of fluid.

Thus, for maximum effectiveness of the superabsorbent polymers, absorbent structures which include such materials in particulate form preferably maintain separation of the particles from one another to permit maximum absorption and swelling without allowing the particles to coalesce and form a gel barrier.

Prior art particle distribution techniques such as those described earlier herein have not been successful in providing substantially uniform distribution of the particulate superabsorbent polymer when employed on converting lines which are typically utilized to construct absorbent fibrous core structures at speeds of over 500 feet per minute.

OBJECTS OF THE INVENTION

Accordingly, it is an object of the present invention to provide method and apparatus which will uniformly distribute discrete particles along a predetermined portion of the uppermost surface of a moving porous web so that the particles occupy less than 100% of said predetermined portion of the uppermost surface of the moving web.

It is another object of the present invention to provide such method and apparatus which will permit the distribution of particulate onto a moving first porous web and thereafter securement of the distributed particulate in position by combining said first porous web with a second web, thereby encapsulating said distributed particulate between said first and second webs.

It is still another object of the present invention to provide method and apparatus whereby particulate may be uniformly distributed onto any desired number of parallel moving porous webs positioned over one another, and a laminate structure thereafter created by passing said webs either simultaneously or sequentially through one or more sets of combining rolls, such as three-dimensional embossing rolls, to maintain the particulate in its substantially uniformly distributed condition intermediate the respective webs.

SUMMARY OF THE INVENTION

In a particularly preferred embodiment, the present invention comprises method and apparatus for substantially uniformly distributing a layer of discrete particles along a predetermined portion of the uppermost surface of a moving porous web so that the particles occupy less than 100% of the predetermined portion of the uppermost surface of said moving web. The method preferably comprises the steps of
  (a) entraining the particles into a moving gaseous stream;
  (b) passing the gaseous stream through a conduit having a discharge end with a nozzle exit positioned adjacent the uppermost surface and oriented so as to discharge the gaseous stream containing said entrained particles in a direction substantially parallel to the direction of travel of the moving porous web;
  (c) mixing the particles entrained in the gaseous stream inside the conduit to provide a substantially uniform distribution of the particles, as measured across the width of the nozzle exit of said conduit in a direction perpendicular to the direction of travel of said moving porous web;
  (d) discharging the gaseous stream containing the uniformly distributed entrained particles from the conduit adjacent the predetermined portion of the uppermost surface of the moving porous web; and
  (e) maintaining the fluid pressure adjacent the lowermost surface of the moving porous web at a level lower than that adjacent the uppermost surface of the web in an area coinciding in width to the predetermined portion of the web, said area being located near the nozzle exit of the conduit, whereby the bulk of the uniformly distributed particles entrained in the discharged gaseous stream are substantially uniformly deposited onto the predetermined portion of the uppermost surface of the moving porous web as the bulk of the gas in the gaseous stream is drawn from the uppermost to the lowermost surface of said porous web.

In a particularly preferred embodiment, a second porous web is thereafter superposed over said first web and the uniformly distributed particles deposited thereon and the two porous webs are passed simultaneously between a pair of mating embossing rolls to three-dimensionally expand and fix the pair of webs to one another by fibrous entanglement, thereby substantially locking the particulate in a uniformly distributed condition between the webs.

In still another preferred embodiment of the present invention, recycling apparatus is provided at the lateral edges of the first porous web to collect any particulate which is not deposited directly onto the uppermost surface of the first moving porous web and to recycle the particulate thus collected back to the particle entrainment portion of the system. A similar recovery system may, if desired, be employed for particulate pulled completely through the porous web. This not only minimizes losses which would otherwise be encountered during the particle distribution operation, but provides a more dust-free and sanitary operating environment.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE PRESENT INVENTION

While the present invention will be described in detail in the context of providing an absorbent laminate structure for use as an absorbent core in an absorbent bandage such as a disposable diaper, the present invention is in no way limited to such application. For example, the present invention may be employed with equal facility to provide a substantially uniform, but spaced distribution of superabsorbent polymer particles on the uppermost surface of a porous three-dimensional absorbent batt for later incorporation into disposable absorbent structures such as diapers and sanitary napkins.

Figure 1:
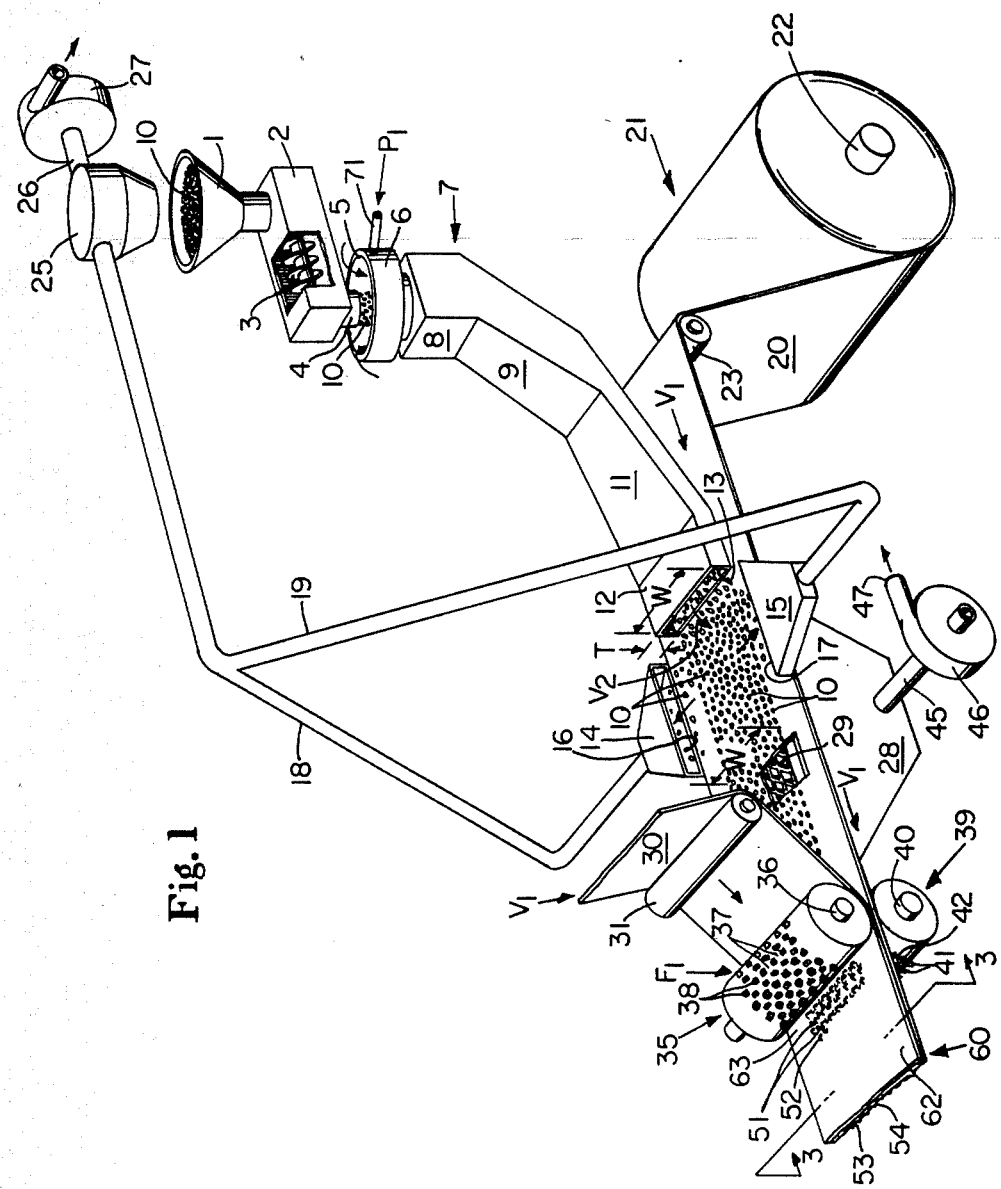
FIG. 1 is a simplified perspective representation of preferred particle distribution and three-dimensional embossing apparatus of the present invention.

FIG. 1 discloses a particularly preferred system for constructing a two-layer laminate having discrete particles of superabsorbent polymer substantially uniformly distributed along a predetermined portion of its width. In the embodiment illustrated in FIG. 1, a first porous web 20 is delivered from a powered supply roll 21 supported on shaft 22 to a first idler roll 23 which preferably extends across the width of the entire web 20.

Web 20 is preferably comprised of a porous material which is preferably fibrous in nature. It is most preferably comprised of thin, substantially contiguous material having two substantially parallel surfaces. Although the web of porous material, as used herein, need not be flat or smooth, it is or can be laid out in a substantially planar, two-dimensional arrangement of indefinite length and indefinite width projecting in these two dimensions. The direction perpendicular to the substantially planar, two-dimensional arrangement of such a web of material will be referred to herein as the Z-direction of the web of material. The Z-direction structure of the webs of fibrous materials is an important attribute of the resultant layered absorbent structure described herein.

A web of porous material as used herein may be considered to have a true thickness and an apparent thickness. The true thickness of such a web of material is the distance between its two substantially parallel surfaces. Because the webs are preferably comprised of fibrous materials, the microscopic surfaces of the webs of material are very irregular. Therefore, when the surfaces of these webs are described as substantially planar, the webs are being viewed on a macroscopic scale. The surfaces of the webs are also described as substantially parallel; this does not mean that the webs cannot have thick and thin areas and even some discontinuous areas, e.g., holes. Instead, substantially parallel surfaces, as used herein, means that when there is a substantial macroscopic change of direction of one surface of a web of material, the other surface of the web makes a substantially parallel change of direction.

Examples of porous webs used in absorbent bandages of the type herein described include many papers and non-woven materials. The webs of fibrous materials used in practicing of the present invention are preferably webs of absorbent materials, more preferably webs of absorbent papers, more preferably still webs of absorbent tissues. The webs of fibrous materials of a layered absorbent structure of the type generally disclosed herein may all be the same fibrous material or may be different fibrous materials.

In yet other embodiments of the present invention, the porous web on which the particles are deposited may comprise a layer of airlaid comminuted wood pulp fibers or the like. Depending upon the cohesive strength of the particular absorbent web selected, it may be necessary to utilize traveling support means, such as a foraminous belt, or a tissue ply to convey the absorbent web during the particle distribution process. Situations of this type may or may not involve laminating of multiple webs to produce an absorbent core structure. For example, it may be sufficient to provide uniformly distributed superabsorbent polymer particles throughout the uppermost region of a conventional absorbent web, such as a layer of airlaid comminuted wood pulp fibers. Such a structure provides the ability to substantially instantaneously contain and temporarily store large volumes of rapidly discharged fluid within the void volume of the airlaid web. This ability to quickly contain and temporarily store rapidly discharged fluid, minimizes run-off and provides sufficient exposure time to effectively utilize the very large total absorbent capacity of the superabsorbent polymer particles which tend to absorb the fluid from the void volume of the airlaid web. This combination of properties is particularly desirable in structures such as disposable diapers where urine is rapidly and periodically discharged over the entire useful life of the structure.

If desired, an additional web of similar or dissimilar type may be superposed on the first web after the particles have been distributed thereon.

Particularly preferred webs of absorbent tissue for making a layered absorbent structure of the type generally disclosed in the Drawing Figures exhibit a basis weight of from about 10 grams per square meter to about 100 grams per square meter, more preferably from about 15 grams per square meter to about 40 grams per square meter.

In the embodiment disclosed in FIG. 1, the porous web 20 is fed from idler roll 23 across a particle deposition zone comprising a suction chamber 28 having an uppermost lattice type support grid 29. The lattice type support grid 29 exhibits a pattern of openings or apertures which will permit a pre-determined portion of the web having a width "W" to be exposed to a fluid pressure differential at some point during its traverse of the vacuum chamber 28. Because of the porous nature of the web 20, vacuum blower 46 which is connected to vacuum chamber 28 via conduit 45 draws air and gas present adjacent the uppermost surface of the porous web 20 through that predetermined portion of the web corresponding to width "W" and discharges it through exhaust port 47, as generally shown in FIG. 1. Thus the fluid pressure differential created by vacuum blower 46 causes the particles 10 entrained in the gaseous stream adjacent the uppermost surface of porous web 20 to be deposited on that portion of the web corresponding to width "W" when the gas is drawn through the web.

The absorbent particles 10 used in layered absorbent structures of the type disclosed herein may be any fluid absorbent material that swells when it absorbs fluid. It is highly preferred that the absorbent particles be water insoluble polymeric materials (superabsorbent polymers) having a water absorption capacity of 15 times their dry weight or more, preferably having a water absorption capacity of 30 times their dry weight or more, more preferably having an aqueous saline solution absorption capacity of 30 times their dry weight or more of a solution of 1% sodium chloride in water.

There is a wide variety of materials which are or can be physically structured to perform as superabsorbent polymers. Although the following list is not meant to be inclusive of all superabsorbent polymers, such materials are disclosed in the following U.S. Pat. Nos.: 2,798,053 issued to Brown on July 2, 1957; 2,988,539 issued to Cohen, Spaulding & Jones on June 13, 1961; 3,220,960 issued to Wichterle & Lim On Nov. 30, 1965; 3,247,171 issued to Walker & Pillepich on Apr. 19, 1966; 3,393,168 issued to Johnson on July 16, 1968; 3,419,006 issued to King on Dec. 31, 1968; 3,425,971 issued to Gugliemelli, Weaver & Russell on Feb. 4, 1969; 3,514,419 issued to Darlow & Gibb on May 29, 1970; 3,628,534 issued to Donohue on Dec. 21, 1971; 3,661,815 issued to Smith on May 9, 1972; 3,664,343 issued to Assarsson on May 23, 1972; 3,669,103 issued to Harper, Bashaw & Atkins on June 13, 1972; 3,670,731 issued to Harmon on June 29, 1972; 3,783,872 issued to King on Jan. 8, 1974; 3,810,468 issued to Harper, Bashaw & Atkins on May 14, 1974; 3,926,891 issued to Gross & McFadden on Dec. 16, 1975; 3,935,099 issued to Weaver, Bagley, Fanta & Doane on Jan. 27, 1976; 3,954,721 issued to Gross on May 4, 1976; 3,971,379 issued to Chatterjee on July 27, 1976; 3,980,663 issued to Gross on Sept. 14, 1976; 3,993,553 issued to Assarsson & King on Nov. 23, 1976; 3,997,484 issued to Weaver, Bagley, Fanta & Doane on Dec. 14, 1976; 4,017,653 issued to Gross on Apr. 12, 1977; 4,018,951 issued to Gross on Apr. 19, 1977; 4,044,766 issued to Kaczmarzyk, Hlaban & Bernardin on Aug. 30, 1977; 4,045,387 issued to Fanta & Doane on Aug. 30, 1977; 4,051,086 issued to Reid on Sept. 27, 1977; 4,058,124 issued to Yen & Osterholtz on Nov. 15, 1977; 4,076,673 issued to Burkholder, Jr. on Feb. 28, 1978; 4,090,013 issued to Ganslaw & Katz on May 16, 1978; 4,093,776 issued to Aoki & Yamasaki on June 6, 1978; 4,102,340 issued to Mesek & Repke on July 25, 1978; 4,105,033 issued to Chatterjee & Morbey on Aug. 8, 1978; 4,117,184 issued to Erickson & Krajewski on Sept. 26, 1978; 4,190,562 issued to Westerman on Feb. 26, 1980; 4,200,557 issued to Chatterjee & Schwenker, Jr. on Apr. 29, 1980; and 4,232,674 issued to Melican on Nov. 11, 1980.

Particularly preferred superabsorbent polymers for use in layered absorbent structures of the type herein disclosed comprise saponified starch-polyacrylonitrile graft copolymers, starch-polyacrylic acid graft copolymers, cross-linked/grafted cellulose, saponified vinyl acetate-acrylic acid copolymers, starch grafted polyvinyl acetate, acrylic acid polymers, cross-linked polyethylene oxide, and the like. The superabsorbent polymer particles used in such structures may all be the same or a mixture of different superabsorbent polymers.

In the absorbent laminate structures disclosed in the Drawing Figures, absorbent particles 10 are preferably incorporated as a discontinuous layer between webs of porous materials. The absorbent particles 10 may be in a form such as flakes, powders, or granules. Particularly preferred superabsorbent polymer particles comprise flakes or granules.

In the resultant absorbent structures, it is preferable to minimize the amount of absorbent particles 10 that can substantially shift position in or escape from the absorbent structure. Therefore, the particles are preferably larger than any openings in the porous webs. In addition to minimizing particle loss in the resultant absorbent structure, this helps to ensure rapid and even particle distribution on the uppermost surface of the porous web during the deposition process, since the larger particles cannot pass through the web.

To minimize waste in practicing the present invention, it is particularly preferred that any particles drawn through the porous web 20 during the deposition process be collected and recycled to the infeed end of the particle handling system.

For absorbent structures where the preferred absorbent tissues are used as the webs of fibrous materials, it is preferred that the size distribution of the particles be such that about 90% (by weight) or more of the particles comprise two perpendicular dimensions of from about 0.05 mm to about 1.0 mm, more preferably such that about 70% (by weight) or more of the particles comprise two perpendicular dimensions of from about 0.15 mm to about 0.6 mm. Many absorbent structures disclosed in the references cited hereinbefore are comprised of layered webs of fibrous materials with superabsorbent polymer particles between the web layers. One reason the superabsorbent particles are incorporated in such structures is because they have a greater water absorbing capacity per gram than conventional absorbent fibrous materials. Because of this greater absorbing capacity of the superabsorbent polymer particles, such absorbent structures can be made thinner, less bulky and lighter in weight than absorbent structures made entirely from conventional absorbent fibrous materials. Such thinner, less bulky, lighter weight absorbent structures provide potential benefits when incorporated in absorbent bandage products such as disposable diapers, disposable incontinent briefs, sanitary napkins, wound and/or surgical dressings, and the like.

For such absorbent products, the absorbing capacity of the product is a primary concern. However, the rate of absorption of fluid is also generally of importance for such products. Disposable diapers, incontinent briefs, and catamenial products, in particular, must be capable of handling gushes of fluid in short periods of time. In the layered absorbent structures disclosed herein, a primary function of the webs of porous materials is to initially absorb the gushes of fluid and transport the fluid to the superabsorbent polymer particles for absorption and retention of them. Thus the webs of fibrous materials preferably have sufficient void volume to handle such gushes of fluid and good wicking properties to quickly disperse the fluid throughout the absorbent structure and to the absorbent particles constrained between the webs. Absorption of the fluid from the fibrous materials by the superabsorbent polymer particles regenerates the absorbing capacity of the fibrous material so that it is capable of absorbing additional gushes of fluid.

A rapid absorption of the fluid by the superabsorbent particles is desired. The rate of absorption of fluid by the particles is, of course, dependent on the superabsorbent polymer employed; however, it is also dependent on the physical attributes of the particles and their relationship to the webs of fibrous materials. The rate of absorption of fluid by such a particle is proportional to the surface area of the particle exposed to the fluid being absorbed. Therefore, a maximum absorption rate is achieved by the particle when it is surrounded by the fluid being absorbed. This can be accomplished in layered absorbent structures of the present invention if each particle is surrounded by the fibrous material which transports the fluid to the particle.

As superabsorbent polymer particles absorb fluid, they swell substantially. Such a particle will exhibit its maximum rate of absorption and maximum absorbing capacity if it is free floating, totally unconstrained in the fluid being absorbed. If such particles are constrained such that they are not free to swell in an uninhibited manner, either the rate of absorption of fluid by the particle, or the capacity of the particle to absorb fluid, or both, will be adversely affected. The absorption rate and/or capacity of many commercially available superabsorbent polymer particles are adversely affected by process conditions which affect their structure, particularly those involving wetting and drying, excessive heating, excessive pressure, or direct contact with adhesives. Such process steps, particularly those which involve the wetting and drying of the particles, can also increase the cost of making layered absorbent structures.

If the superabsorbent polymer particles 10 in an absorbent structure are constrained such that they are in contact with one another, both the rate of absorption and absorption capacity of the particles will be adversely affected. If the particles are in contact with one another, fluid cannot totally surround each particle, and its maximum rate of absorption cannot be achieved. As the contacting particles absorb fluid and begin to swell, they are not free to swell to their fullest extent because of their contact with one another; thus they are unable to achieve their maximum absorbing capacity. Also, as such contacting particles absorb water and swell, they will often coalesce to form a gel layer which may block the flow of fluid to other particles, thus reducing the absorption rate and capacity of the structure as a whole. It is therefore preferable to have the superabsorbent polymer particles separated within a layered absorbent structure with sufficient spacing between the particles to allow them to swell to their maximum size without contacting neighboring particles.

It is therefore preferable that particles 10 are spaced sufficiently far enough from one another that if the resultant layered absorbent structure is subsequently wetted by a fluid such that particles 10 absorb the fluid and swell to saturation, the saturated particles would cover less than 100% of the surface area of each of the interfaces between the superposed webs; more preferably the saturated particles would cover less than 90% of the surface area of each of said interfaces. Such a dispersed spacing of absorbent particles is preferred to ensure that even when the absorbent particles are saturated with fluid and swollen, there is still room between the swollen particles for fluid to pass through all the layers of the absorbent structure. This enables fluid to freely transport through such absorbent structures until it contacts and is absorbed by absorbent particles which are unsaturated.

Since many superabsorbent polymer particles swell such that their dimensions when saturated with fluid are double or more their dry dimensions, it is preferred that such dry particles cover no more than 50% of the surface area of each of said interfaces; more preferably that the particles cover no more than 20% of the surface area of each of the interfaces.

The foregoing targets for substantially uniform particle distribution within a predetermined portion of the uppermost surface of the porous web 20 can be achieved in accordance with the process generally disclosed in FIG. 1. In particular, the superabsorbent polymer particles 10 are fed from a bulk hopper 1 into a horizontal chamber in which is mounted a continuously rotating auger 3 which advances the particles 10 along the length of chamber 2 and discharges them by gravity out discharge conduit 4. The speed of rotation of the auger 3 determines the rate of particle flow through discharge conduit 4.

Upon discharge from conduit 4, the particles 10 are entrained in a fast moving stream of air. In the illustrated embodiment, this is accomplished by discharging the metered particles 10 into an eductor 6 such as a Vortec Model No. 913 available from Vortec Corporation of Cincinnati, Ohio. The eductor 6 contains an internally located, circumferential slot 5 having a downwardly projecting orientation. The internally located, downwardly projecting, circumferential slot 5 is connected to a pressure source, such as an air compressor (not shown), via conduit 71 which supplies compressed gas, preferably air, at a regulated pressure $P_1$. Thus the eductor provides an internal, downwardly directed flow of gas about the interior peripheral edge of the slot 5. The downwardly projecting gas flow issuing from the circumferential slot 5 draws ambient air from about the periphery of the eductor 6 and discharges it, along with the uniformly distributed entrained particles 10, at the nozzle exit 13 of distribution conduit 7, as generally shown in FIG. 1. Use of the eductor 6 permits a substantially constant volume of particles 10 to be metered into the distribution conduit 7 without air disturbance of the particle metering system.

The eductor 6 is preferably sized to provide an adequate CFM (cubic feet per minute) rating at nozzle exit 13 at reasonably available compressed air pressures. For any particular application, the CFM requirements are dependent upon the cross-sectional area of the nozzle exit 13 of distribution conduit 7 and the velocity needed to effectively transport the particular particles 10 being spread. For small lightweight particles 10, i.e., superabsorbent polymer particles of the type generally described herein, a nozzle exit velocity $V_2$ in the range of about 2,000–3,000 feet per minute is typically sufficient. For higher flow rates (approaching dense flow) and more dense particles, higher velocities are generally found to work better. In addition to the foregoing, the size of the eductor is also determined by output area considerations of the distribution conduit 7. Since continual cross-sectional area reduction is required throughout the traverse of the discharge conduit 7, the cross-sectional flow area existing at the slot 5 of the eductor 6 is preferably about double the cross-sectional flow area at nozzle exit 13.

As can be seen in the embodiment shown in FIG. 1, distribution conduit 7 preferably comprises discrete straight segments 8, 9, 11 and 12 which convert the direction of particle discharge from vertical at the point of introduction to the eductor 6 to substantially horizontal and parallel to the uppermost surface of moving web 20 at nozzle exit 13. Close coupling the vertically metered particles 10 with a nozzle exit 13 oriented parallel to a horizontally oriented, moving web not only minimizes turbulence, which could otherwise cause particle surging inside the conduit 7, but also minimizes the incidence of particle bounce at the web which typically results when the particles are discharged in a direction substantially perpendicular to the direction of web travel.

In the illustrated embodiment, the direction of the particles 10 is changed from substantially vertical to substantially horizontal by means of lowermost sections 9, 11 and 12 of distribution conduit 7, each of the three segments involving a 30° angle change to provide a 90° reorientation of the particle flow. The 30° straight sections provide riffling surfaces to spread particles by gravity as well as by airflow. As particles change direction at the 30° bends, they tend to spread. However, gravity and centrifugal force cause the particles to impact against the bottom side of the conduit 7 and thereby enhance the spreading action of the particles across the entire width of the nozzle.

In a particularly preferred embodiment of the present invention, a 10 to 15% gas velocity increase occurs with each 30° angle change to prevent particle makeup in the corners of the distribution conduit 7.

Thus, through each discrete straight segment, i.e., segements 8, 9 and 11, the cross-sectional area, as measured in a direction substantially perpendicular to flow, decreases slightly so that the air velocity is increased slightly over the length of the segment. However, a 25–50% area reduction preferably occurs over segment 12 to create the primary pressure drop at nozzle exit 13. This is done to compensate for the fact that particles issuing from either lateral extremity of nozzle exit 13 must traverse a longer path in conduit 7 than particles issuing from the center of nozzle exit 13. The longer path at the lateral extremities of conduit 7 produces a greater pressure drop and would reduce air velocity at the lateral extremities of the nozzle exit if the primary drop were not at the point of discharge. Thus, the higher air velocity, and hence the higher pressure differential, existing at nozzle exit 13 as a result of the reduction in cross-sectional area promotes uniform air and particle flow across the full width "W" of the nozzle exit.

For flow rates from about 5 to about 25 grams per second using particles 10 having a maximum density on the order of about 0.7 grams per cubic centimeter and a maximum size of about 1,000 microns, the nozzle exit height "T" is preferably at least ⅛ inch high, regardless of its width "W" so that particle clogging is prevented.

As will be apparent from FIG. 1, the latter portion of conduit 7, i.e., segment 12, employs straight sidewalls aligned substantially parallel to the lateral edges of the moving web 20. This provides parallel flow of the uniformly distributed gas/particle stream which issues from nozzle exit 13 at velocity $V_2$. In order to ensure that the gas/particle flow does not spread in a direction perpendicular to the nozzle exit 13, straight segment 12 of conduit 7 has sidewalls with a length at least 8 times the height "T" of the nozzle exit, as measured in the direction of particle flow.

As will be appreciated by those skilled in the art, the maximum included spreading angle in conduit 7, as viewed from overhead, should not exceed about 30° in order to prevent sidewall turbulence. For a given nozzle exit width "W", smaller included angles work better since they result in a longer nozzle with more overall length and consequently more opportunity for riffling of the particles 10 to occur.

If desired, the conduit 7 can be vibrated (by means not shown) to further enhance particle distribution and to avoid particle hang-up within the conduit.

Using the process and apparatus disclosed in FIG. 1, small volumes of superabsorbent particles 10 of the type generally described herein can be spread onto a predetermined portion corresponding to width "W" of the uppermost surface of a porous tissue paper web 20 so as to occupy less than 100% of the predetermined portion of said web. For example, at a web speed $V_1$ of 100 feet per minute, the flow rate of said superabsorbent particles 10 to be spread out over a 12 inch wide portion of the web may be as low as 1 gram per second.

Since the nozzle discharge velocity $V_2$ is typically in the 2,000 to 4,000 foot per minute range, the particle spreading process herein disclosed is not speed limited. This spreading process has been successfully demonstrated on superabsorbent polymer particles of the type generally described herein at a web speed $V_1$ in the range of 50 to 1,000 feet per minute. Due to web handling limitations, the required particle conveying velocity $V_2$, as measured at nozzle exit 13, is typically greater than the velocity $V_1$ of the web. However, given suitable web handling means, a web velocity $V_1$ approaching, equaling or even exceeding the particle velocity $V_2$ is believed feasible in practicing the present invention.

High speed photography has been utilized to verify that the particle discharge at the nozzle exit 13 is uniformly distributed across the width W of the nozzle. Furthermore, the aforementioned high speed photography analysis has demonstrated that known pulsations introduced from the auger actuated metering system are somewhat dampened out in the lateral spreading process which takes place in distribution conduit 7.

As can be observed from FIG. 1, the particles 10 entrained in the gaseous stream discharged at velocity $V_2$ from nozzle exit 13 of conduit 7 are deposited onto that portion of the uppermost surface of porous web 20 corresponding to width "W" by drawing the gas contained in the stream through the porous web 20. This is preferably accomplished by maintaining a negative pressure within chamber 28, such that the bulk of the gas in the stream discharged from nozzle exit 13 is drawn into chamber 28 through porous web 20 and lattice type support grid 29 via conduit 45 and blower 46 which thereafter ejects the gas through discharge conduit 47. In a particularly preferred embodiment of the present invention, the overall length of the chamber 28 and the lattice type support grid 29 as measured in the direction of web travel, is approximately two feet and is positioned so that its leading edge coincides with nozzle exit 13.

It is of course recognized that particles 10 which are smaller in size than the pores in the web 10 may be drawn through the web 10 along with the gas. If desired, these could be removed by means of a cyclone type separator (not shown) and returned to the particle infeed hopper 1.

In an exemplary embodiment of the type herein described in relation to FIG. 1, approximately 40 CFM of air are removed from the gaseous stream by blower 46. The vacuum thus created inside chamber 28 not only prevents the porous web 20 from developing wrinkles, but helps to prevent excess air from blowing particles 10 out the sides of the tissue layer 20. It also tends to stabilize the particles in the position in which they are initially deposited until a secondary porous web 30, which may be identical to porous web 20, is fed about idler roll 31 and into converging relation with porous web 20 at mating embossing rolls 35 and 39.

The process illustrated in FIG. 1 is particularly suitable for producing a layered absorbent structure for use in disposable absorbent bandages such as diapers, incontinent pads, sanitary napkins, and the like. For such an absorbent structure, web 30 is preferably a porous web generally similar to porous web 20. Webs 20 and 30 are both fed into the nip between mating embossing rolls 35 and 39 at velocity $V_1$. The uppermost surface of web 20 has a predetermined portion of width W over which is distributed a substantially even, but discontinuous layer of particles 10. The predetermined portion of web 20 exhibits a width "W" corresponding in width to that of chamber 28 and nozzle exit 13.

Although the bulk of the particles 10 initially entrained in the gaseous stream which issues from nozzle exit 13 at velocity $V_2$ are collected on the uppermost surface of porous web 20, a recycling system is preferably employed to provide a sanitary working environment and to avoid waste of any particles 10 which do not find their way into contact with the predetermined portion of porous web 20. In the illustrated embodiment, any particles 10 which do not deposit onto the predetermined centrally located portion of porous web 20 are collected by a pair of vacuum nozzles 14 and 15 via their inlet ports 16 and 17, respectively. Vacuum nozzles 14 and 15 are preferably connected via conduits 18 and 19, respectively, to a cyclone type separator 25, such as a Ducon Series "VM", Model 700, as available from Ducon Company of Mineola, Long Island, N.Y. In the separator 25 the air is separated from the particles 10 and the particles are deposited back into the bulk hopper 1 for recycling to the particle deposition zone. Air which is separated from the stream is drawn through conduit 26 by blower 27 and is ultimately discharged to the atmosphere through a filter (not shown). Thus, the deposition process described herein wastes little or none of the often expensive particles 10.

Webs 20 and 30 with discontinuous layer of particles 10 located therebetween in a predetermined portion of width "W" are preferably crimped together to form a laminate structure 60 by means of rolls 35 and 39 which have mating Z-direction geometrical protrusions and concavities. As can be generally seen from FIG. 1, the outer cylindrical crimping surfaces of rolls 35 and 39 have multiple identical Z-direction protrusions, i.e., protuberances 38 and 41, respectively. In the illustrated embodiment, the protrusions are all substantially square based pyramids. Each square based pyramid meshes with a corresponding concavity on the surface of the opposite roll; therefore, the mating Z-direction concavities mesh with the protuberances on the opposite roll.

Figure 3:
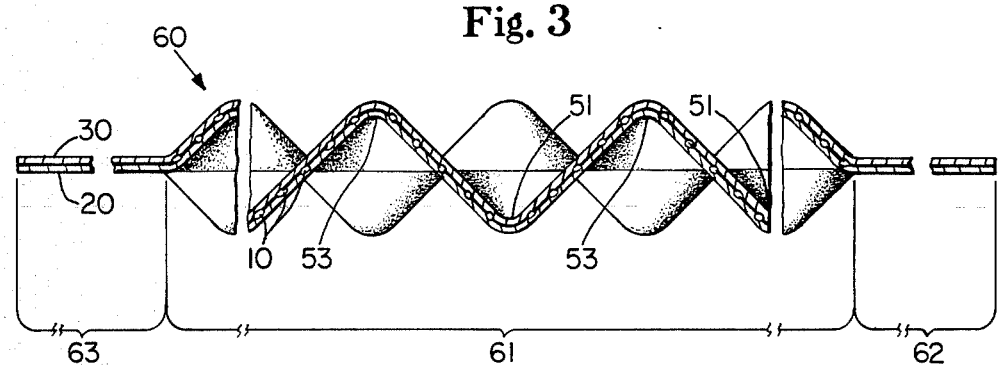
FIG. 3 is an enlarged cross-sectional illustration of a two-layer laminate structure of the type generally disclosed in FIG. 1, said cross-section being taken along section line 3—3 of FIG. 1.

FIG. 3 is a simplified, greatly enlarged cross-sectional illustration of absorbent laminate structure 60 taken along section line 3—3 of FIG. 1. In the illustrated embodiment only the centrally located portion 61 of the laminate having a width "W" has been three-dimensionally embossed by rolls 35 and 39, while the peripheral edges 62 and 63 remain in a substantially planar, undeformed condition. It is of course recognized that the width "W" of the nozzle exit 13, the particle deposition zone and/or the embossing rolls may be any desired dimension up to and including the entire width of web 20 and/or web 30. The latter situation may in fact be preferred in situations involving rewinding of the resultant laminate structure 60.

The protrusions 38 on embossing roll 35 correspond to the valleys 51 located on the uppermost surface of the absorbent laminate structure 60, while the protrusions 41 on roll 39 correspond to the peaks 53 on the lowermost surface of the absorbent laminate structure.

As a result of the substantially uniform distribution of particles 10 across the predetermined portion of width "W" of porous web 20, the crimping action imparted to webs 20 and 30 by simultaneous passage between rolls 35 and 39 effectively fixes the particles in spaced relation to one another at the interface of the two webs. The fibrous entanglement of the three-dimensionally expanded webs provides a frangible bond between the web surfaces that will permit the discrete absorbent particles 10 to swell in a substantially uninhibited manner when contacted by liquid. This, in combination with the discrete separation of the particles 10 from one another assures that the full absorptive capacity of the particles can be effectively utilized without gel blockage or physical constraint.

As will be appreciated, the strength of the bond between opposed adjacent surfaces of webs 20 and 30 will depend upon such factors as the number and shape of the intermeshing Z-direction protrusions and concavities, the surface properties of the webs of materials 20 and 30, and the density of the absorbent particles at the interfaces between the webs.

In general, a greater number of such protrusions and concavities having a given height, or a higher height of such protrusions having a given base width will result in a stronger bond between opposed adjacent surfaces of adjacent webs. In a particularly preferred embodiment, a density of about 16 protrusions per square centimeter of laminate web surface has been found effective. Using the length of one side of the square base of the pyramidal shaped protrusions as the base width of the protrusion, the height to base width ratio of the protrusions of crimping surfaces of the respective rolls 35 and 39 is preferably about 1.1 to 1.

Although the configuration of crimping surfaces shown in FIG. 1 are preferred, an almost infinite variety of protrusion and concavity shapes and patterns could be provided in order to produce the desired intermeshing Z-direction protrusions and concavities in layered absorbent structures of the type herein disclosed. It is particularly preferred that at least one of such surfaces have from about 10 to about 50 protrusions per square centimeter, more preferably from about 15 to about 25 protrusions per square centimeter. It is preferred that the Z-direction height of such protuberances be from about 1 millimeter to about 5 millimeters, more preferably from about 2 millimeters to about 3 millimeters. It is preferred that such protrusions taper substantially entirely from their base to their tip. The preferred protrusions are pyramidal or conical shaped; however, a large variety of shapes which would be suitable can readily be conceived by a skilled artisan. Processes of the present invention are not limited to any particular size or shape of protrusion or concavity.

If desired, the strength of the bond between opposed adjacent surfaces of webs 20 and 30 can be further increased by passing the laminate structure 60 between a pair of low pressure calender rolls (not shown). However, the increased bond strength is normally accompanied by some reduction in Z-direction caliper from the laminate structure's initially crimped condition.

Layered absorbent structures comprised of more than a single pair of porous webs have been found effective for use in various disposable absorbent structures. An exemplary process of the present invention for producing a three-layer structure is generally disclosed in FIG. 2. In the simplified schematic illustration disclosed in FIG. 2, the system generally disclosed in FIG. 1 is first utilized to form a two-layer absorbent laminate structure 160 which is thereafter fed about idler rolls 270, 271, and 272 in an S-wrap configuration to yet another idler roll 231 which aligns the two-layer laminate structure 160 for feeding toward a secondary pair of embossing rolls 235 and 239. The latter are generally similar to rolls 35 and 39, respectively. However, in the embodiment disclosed in FIG. 2, a secondary particle feeding system comprising hopper 201, horizontal conduit 202, continuously rotating auger 203 and discharge conduit 204, all generally similar to the corresponding elements shown in FIG. 1, is also employed.

Figure 2:
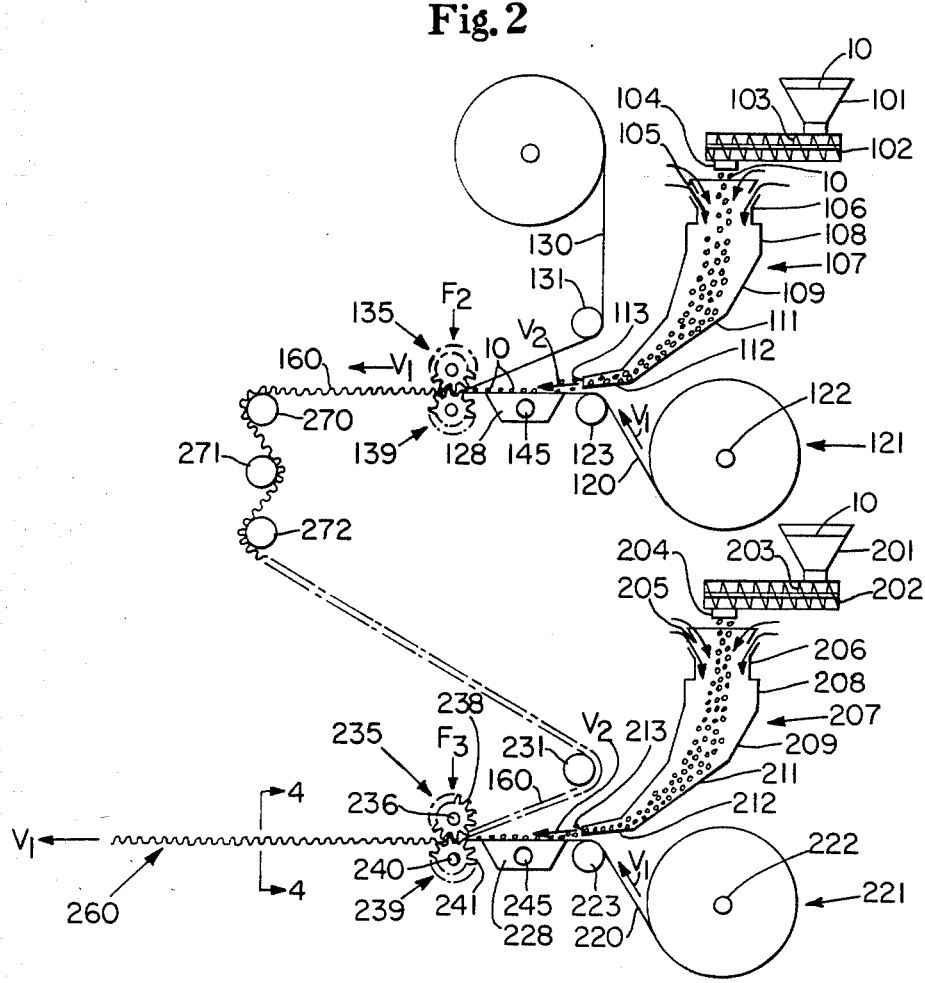
FIG. 2 is a simplified schematic illustration of method and apparatus for substantially uniformly distributing particulate intermediate the layers of a three-layer laminate structure in accordance with the present invention.

As can be seen from FIG. 2, particles 10 are fed into an eductor 206 having a circumferential slot 205 which is also supplied by a source of compressed gas at pressure $P_1$. These elements are generally similar to those described in conjunction with the embodiment of FIG. 1. The particles 10 and air from the surrounding atmosphere are distributed throughout conduit 207 which is generally similar to distribution conduit 7 shown in FIG. 1. The particles 10 are uniformly distributed within conduit 207 and are discharged at nozzle exit 213 in a manner generally similar to that disclosed with respect to the embodiment of FIG. 1.

An additional porous web 220, which is preferably similar to porous web 20, is fed from supply roll 221 which is supported by shaft 222. The porous web 220 passes about idler roll 223 and across the surface of a suction chamber 228 generally similar to vacuum chamber 28 shown in FIG. 1. As with the embodiment disclosed in FIG. 1, the gas contained in the gas/particulate stream discharged from nozzle exit 213 is drawn through a predetermined portion of width W of porous web 220 and the particulate 10 is deposited onto said predetermined portion of the uppermost surface of porous web 220.

Porous web 220, with the uniformly distributed particles 10 deposited on its surface, is simultaneously fed at velocity $V_1$ with the top-layer laminate structure 160 into the nip between mating embossing rolls 235 and 239 which are generally similar to rolls 35 and 39, respectively, shown in FIG. 1. Embossing roll 239 supported by shaft 240 is preferably vertically stationary, while embossing roll 235 supported on shaft 236 is preferably vertically movable and adjustably loaded by means of hydraulic or pneumatic cylinders (not shown) which apply equalized forces to opposite ends of shaft 236. As a result of passage between the pressure loaded embossing rolls 235 and 239, a three-layer absorbent laminate structure 260 having particulate 10 substantially uniformly distributed at all of its interfaces is created.

Figure 4:
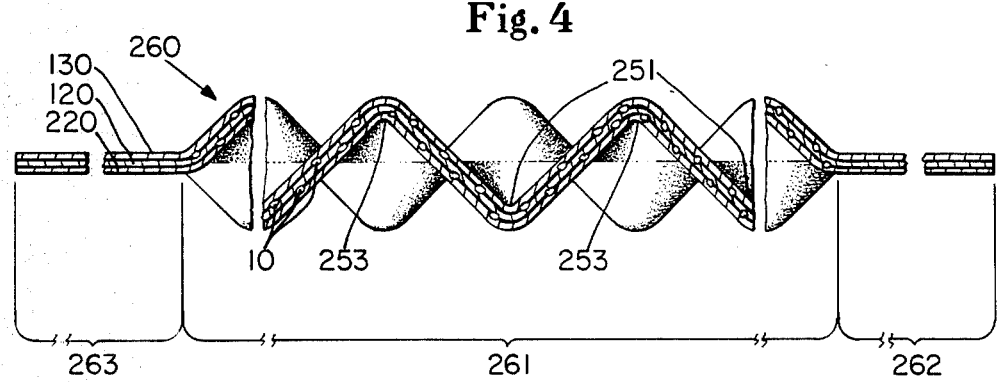
FIG. 4 is an enlarged cross-sectional illustration of a three-layer laminate structure taken at a point corresponding to section line 4—4 of FIG. 2.

FIG. 4, which is an enlarged cross-sectional illustration of absorbent structure 260 taken along section line 4—4 of FIG. 2, discloses an overall cross-sectional appearance generally similar to that of absorbent laminate structure 60. The embossed portion of the structure 261 is centrally located, while the peripheral edges 262 and 263 remain substantially undeformed. The valleys 251 of the absorbent laminate structure correspond to peaks of the protuberances 238 on embossing roll 235, while peaks 253 on the lowermost surface of the structure correspond to peaks of the protuberances 241 on mating embossing roll 239.

As will be appreciated, the process generally disclosed in FIG. 2 may be repeated any number of times to provide the desired number of layers in the resultant laminate structure, the only requirement being that the web or webs onto which the particulate is distributed must be sufficiently porous to permit drawing the gas contained in the gas/particulate stream through the thickness of the web or webs and thereby deposit the entrained particles in a substantially uniformly distribued condition along a predetermined portion of the uppermost porous web.

While particular embodiments of the present invention have been illustrated and described, it would be obvious to those skilled in the art that various changes and modifications can be made without departing from the spirit and scope of the invention. It is intended to cover, in the appended claims, all such modifications and contemplated uses.

What is claimed is:

1. A method for substantially uniformly distributing a layer of discrete particles along a predetermined portion of the uppermost surface of a moving porous web traveling at a first velocity so that said particles occupy less than 100% of said predetermined portion of the uppermost surface of said moving web, said method comprising the steps of:

(a) entraining said particles in a moving gaseous stream;

(b) passing said gaseous stream through a conduit having a nozzle exit positioned adjacent the uppermost surface of and oriented so as to discharge said gaseous stream containing said entrained particles in a direction substantially parallel to the direction of travel of said moving porous web;

(c) mixing said particles entrained in said gaseous stream inside said conduit to provide a substantially uniform distribution of said particles, as measured across the width of said nozzle exit of said conduit in a direction perpendicular to the direction of travel of said moving porous web;

(d) discharging said gaseous stream containing said uniformly distributed entrained particles from said conduit adjacent said predetermined portion of the uppermost surface of said moving porous web at a second velocity; and (e) maintaining the fluid pressure adjacent the lowermost surface of said moving porous web at a level below the fluid pressure adjacent the uppermost surface of said moving porous web in an area coinciding in width to said predetermined portion of said web and located near the nozzle exit of said conduit, whereby the uniformly distributed particles entrained in said discharged gaseous stream are substantially uniformly deposited on said predetermined portion of the uppermost surface of said moving porous web as the bulk of the gas in said gaseous stream is drawn from the uppermost to the lowermost surface of said web.

2. The method of claim 1 wherein said gaseous stream and said particles entrained therein undergo a change of direction of approximately 90° as they pass through said conduit.

3. The method of claim 2 wherein the velocity of said gaseous stream and said particles entrained therein increases during their passage through said conduit.

4. The method of claim 3 wherein said increased velocity results from a decrease in cross-sectional flow area, as measured in a direction substantially perpendicular to the direction of flow, said decrease in flow area occurring between the inlet to said conduit and the nozzle exit of said conduit.

5. The method of claim 1 wherein said second velocity of said gaseous stream and said particles entrained therein is greater than said first velocity of said moving porous web, as measured at the nozzle exit of said conduit.

6. The method of claim 1 wherein the fluid pressure adjacent the lowermost surface of said moving porous web is subatmospheric.

7. The method of claim 1 including the step of recycling particles which are not deposited on said predetermined portion of the uppermost surface of said moving porous web as the bulk of the gas contained in said gaseous stream is drawn from the uppermost to the lowermost surface of said web.

8. The method of claim 1 wherein mixing of said particles entrained in said gaseous stream while said particles are inside said conduit is carried out as said particles strike the walls of said conduit.

9. The method of claim 1 wherein said moving porous web comprises a three-dimensional absorbent batt and the particles deposited on said predetermined portion of the uppermost surface of said moving porous web become entangled in the lattice of said web.

10. The method of claim 1 wherein said moving porous web comprises a paper tissue ply.

11. The method of claim 1 wherein said moving porous web comprises a nonwoven material.

12. The method of claim 1, including the step of superposing a second web on said first moving porous web after said particles have been substantially uniformly deposited on said predetermined portion of the uppermost surface of first moving porous web.

13. The method of claim 12, including the step of three-dimensionally embossing said first and second webs to secure them to one another and fix the position of said uniformly distributed particles therebetween.

14. The method of claim 1, including the step of feeding a uniform stream of particles into said moving gaseous stream.

15. The method of claim 14 wherein said uniform stream is provided by means of a rotating auger.

16. The method of claim 1 wherein said particles are entrained in said moving gaseous stream by means of an eductor.

17. The method of claim 1 wherein the width of said nozzle exit corresponds to the width of said predetermined portion of the uppermost surface of said moving porous web onto which said particles are deposited and is in vertical alignment with said predetermined portion of said web.

18. The method of claim 1 wherein said discrete particles are comprised of superabsorbent polymer and are on the average greater in size than the pores in said moving porous web.

19. The method of claim 1 including the step of vibrating said conduit as said gaseous stream and the particles entrained therein pass through said conduit.

20. The method of claim 1 wherein said particles are substantially uniformly distributed onto the predetermined portion of said moving porous web so that they occupy less than 50% of said predetermined portion of the uppermost surface of said moving web.

21. The method of claim 1 wherein the width of said predetermined portion of said moving porous web comprises the entire width of said web.

22. A method for substantially uniformly distributing a layer of discrete particles along a predetermined portion of the uppermost surface of a moving porous web traveling at a first velocity so that said particles occupy less than 100% of said predetermined portion of the uppermost surface of said moving web, said method comprising the steps of:
(a) feeding said particles in a substantially uniform stream to the inlet of a gas eductor;
(b) entraining said particles in a moving gaseous stream;
(c) passing said gaseous stream through a conduit having a nozzle exit positioned adjacent the uppermost surface of and oriented so as to discharge said gaseous stream containing said entrained particles in a direction substantially parallel to the direction of travel of said moving porous web;
(d) mixing said particles entrained in said gaseous stream inside said conduit to provide a substantially uniform distribution of said particles, as measured across the width of said nozzle exit of said conduit in a direction perpendicular to the direction of travel of said moving porous web;
(e) discharging said gaseous stream containing said uniformly distributed entrained particles from said conduit adjacent said predetermined portion of the uppermost surface of said moving porous web at a second velocity which is greater than said first velocity; and
(f) maintaining the fluid pressure adjacent the lowermost surface of said moving porous web at a level below the fluid pressure adjacent the uppermost surface of said moving porous web in an area coinciding in width to said predetermined portion of said web and located near the nozzle exit of said conduit, whereby the uniformly distributed particles entrained in said discharged gaseous stream are substantially uniformly deposited on said predetermined portion of the uppermost surface of said moving porous web as the bulk of the gas in said gaseous stream is drawn from the uppermost to the lowermost surface of said web.

23. The method of claim 22 wherein said gaseous stream and said particles entrained therein undergo a change of direction of approximately 90° as they pass through said conduit.

24. The method of claim 23 wherein the velocity of said gaseous stream and said particles entrained therein increases during their passage through said conduit.

25. The method of claim 24 wherein said increased velocity results from a decrease in cross-sectional flow area, as measured in a direction substantially perpendicular to the direction of flow, said decrease in flow area occurring between the inlet to said conduit and the nozzle exit of said conduit.

26. The method of claim 22 wherein said second velocity of said gaseous stream and said particles entrained therein is at least twice said first velocity of said moving porous web, as measured at the nozzle exit of said conduit.

27. The method of claim 22 wherein the fluid pressure adjacent the lowermost surface of said moving porous web is subatmospheric.

28. The method of claim 22 including the step of recycling particles which are not deposited on said predetermined portion of the uppermost surface of said moving porous web as the bulk of the gas contained in said gaseous stream is drawn from the uppermost to the lowermost surface of said web.

29. The method of claim 22 wherein mixing of said particles entrained in said gaseous stream while said particles are inside said conduit is carried out as said particles strike the walls of said conduit.

30. The method of claim 22 wherein said moving porous web comprises a three-dimensional absorbent batt and the particles deposited on said predetermined portion of the uppermost surface of said moving porous web become entangled in the lattice of said web.

31. The method of claim 22 wherein said moving porous web comprises a paper tissue ply.

32. The method of claim 22 wherein said moving porous web comprises a nonwoven material.

33. The method of claim 22, including the step of superposing a second web on said first moving porous web after said particles have been substantially uniformly deposited on said predetermined portion of the uppermost surface of first moving porous web.

34. The method of claim 33, including the step of three-dimensionally embossing said first and second webs to secure them to one another and fix the position of said uniformly distributed particles therebetween.

35. The method of claim 22 wherein said uniform stream is provided by means of a rotating auger.

36. The method of claim 22 wherein the width of said nozzle exit corresponds to the width of said predetermined portion of the uppermost surface of said moving porous web onto which said particles are deposited and is in vertical alignment with said predetermined portion of said web.

37. The method of claim 22 wherein said discrete particles are comprises of superabsorbent polymer and are on the average greater in size than the pores in said moving porous web.

38. The method of claim 22 including the step of vibrating said conduit as said gaseous stream and the particles entrained therein pass through said conduit.

39. The method of claim 22 wherein said particles are substantially uniformly distributed onto the predetermined portion of said moving porous web so that they occupy less than 50% of said predetermined portion of the uppermost surface of said moving web.

40. The method of claim 22 wherein the width of said predetermined portion of said moving porous web comprises the entire width of said web.

41. An apparatus for substantially uniformly distributing a layer of discrete particles along a predetermined portion of the uppermost surface of a moving porous web traveling at a first velocity so that said particles occupy less than 100% of said predetermined portion of the uppermost surface of said moving web, said apparatus comprising:
(a) means for feeding said particles in a substantially uniform stream to the inlet of a gas eductor;
(b) means for entraining said particles in a moving gaseous stream;
(c) conduit means for passing said gaseous stream through a nozzle exit positioned adjacent the uppermost surface of and oriented so as to discharge said gaseous stream containing said entrained particles in a direction substantially parallel to the direction of travel of said moving porous web;
(d) means for mixing said particles entrained in said gaseous stream inside said conduit to provide a substantially uniform distribution of said particles, as measured across the width of said nozzle exit of said conduit in a direction perpendicular to the direction of travel of said moving porous web;
(e) nozzle exit means at the discharge end of said conduit means for discharging said gaseous stream containing said uniformly distributed entrained particles from said conduit adjacent said predetermined portion of the uppermost surface of said moving porous web at a second velocity which is greater than said first velocity; and (f) means for maintaining the fluid pressure adjacent the lowermost surface of said moving porous web at a level below the fluid pressure adjacent the uppermost surface of said moving porous web in an area coinciding in width to said predetermined portion of said web and located near the nozzle exit of said conduit, whereby the uniformly distributed particles entrained in said discharged gaseous stream are substantially uniformly deposited on said predetermined portion of the uppermost surface of said moving porous web as the bulk of the gas in said gaseous stream is drawn from the uppermost to the lowermost surface of said web.

42. The apparatus of claim 41 wherein said conduit means causes said gaseous stream and said particles entrained therein to undergo a change of direction of approximately 90° as they pass through said conduit.

43. The apparatus of claim 42 wherein said conduit means exhibits a decrease in cross-sectional flow area, as measured in a direction substantially perpendicular to the direction of flow, between its inlet end and its nozzle exit end.

44. The apparatus of claim 43 including means for maintaining the fluid pressure adjacent the lowermost surface of said moving porous web at a subatmospheric level.

45. The apparatus of claim 41 including means for recycling particles which are not deposited on said predetermined portion of the uppermost surface of said moving porous web as the bulk of the gas contained in said gaseous stream is drawn from the uppermost to the lowermost surface of said web.

46. The apparatus of claim 41, including means for superposing another web on said first moving porous web after said particles have been substantially uniformly deposited on said predetermined portion of the uppermost surface of first moving porous web.

47. The apparatus of claim 46, including means for three-dimensionally embossing said first and second webs to secure them to one another and fix the position of said uniformly distributed particles therebetween.

48. The apparatus of claim 41 wherein said means for feeding said uniform stream of particles comprises a rotating auger.

49. The apparatus of claim 41 wherein the width of said nozzle exit corresponds to the width of said predetermined portion of the uppermost surface of said moving porous web onto which said particles are deposited and is in vertical alignment with said predetermined portion of said web.

50. The apparatus of claim 41 including means for vibrating said conduit as said gaseous stream and the particles entrained therein pass through said conduit.

* * * * *

UNITED STATES PATENT AND TRADEMARK OFFICE
CERTIFICATE OF CORRECTION

PATENT NO. : 4,551,191

DATED : November 5, 1985

INVENTOR(S) : Ronald W. Kock and John A. Esposito

It is certified that error appears in the above-identified patent and that said Letters Patent is hereby corrected as shown below:

Column 1, line 37, after "weather.", start a new paragraph.

Column 1, line 49, "therebly" should read -- thereby --.

Column 2, line 16, "At" should read -- As --.

Column 6, line 15, "On" should read -- on --.

Column 6, line 20, "29" should read -- 26 --.

Column 6, line 24, "29" should read -- 20 --.

Column 18, line 30, Claim 37, "comprises" should read -- comprised --.

Signed and Sealed this

Fourth Day of March 1986

[SEAL]

Attest:

DONALD J. QUIGG

Attesting Officer

Commissioner of Patents and Trademarks